United States Patent [19]

Schönafinger et al.

[11] Patent Number: 5,204,475
[45] Date of Patent: Apr. 20, 1993

[54] SUBSTITUTED 3-AMINOSYDNONE IMINES AND SALTS THEREOF

[75] Inventors: Karl Schönafinger, Alzenau; Rudi Beyerle, Frankfurt; Helmut Bohn, Schöneck; Melitta Just, Langen, all of Fed. Rep. of Germany

[73] Assignee: Cassella Aktiengesellschaft, Frankfurt am Main, Fed. Rep. of Germany

[21] Appl. No.: 730,996

[22] Filed: Jul. 16, 1991

[30] Foreign Application Priority Data

Sep. 10, 1990 [DE] Fed. Rep. of Germany ....... 4028679

[51] Int. Cl.$^5$ .................. C07D 413/04; A61K 31/445
[52] U.S. Cl. ..................... 546/210; 546/207; 548/125; 514/326; 514/364
[58] Field of Search ................. 546/207, 210; 548/125; 514/227.8, 326, 364

[56] References Cited

U.S. PATENT DOCUMENTS 3,312,690 4/1967 Masuda et al. ...................... 544/367
3,833,589 9/1974 Simpson ............................... 544/367
4,551,454 11/1985 Schonafinger ....................... 514/252

Primary Examiner—C. Warren Ivy
Assistant Examiner—Celia Chang
Attorney, Agent, or Firm—Perman & Green

[57] ABSTRACT

The invention relates to pharmacologically active substituted 3-aminosydnone imines of the general formula I in which n denotes 0 or 1, and their pharmacologically acceptable salts and acid addition salts, and to a process for the preparation of the compounds according to the invention and their use.

8 Claims, No Drawings

SUBSTITUTED 3-AMINOSYDNONE IMINES AND SALTS THEREOF

The invention relates to pharmacologically active substituted 3-aminosydnone imines of the general formula I

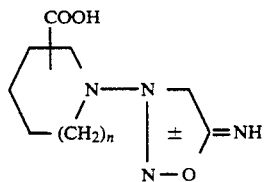

in which n denotes 0 or 1, and their pharmacologically acceptable salts and acid addition salts.

The invention furthermore relates to a process for the preparation of the compounds according to the invention and to their use.

In the general formula I, the carboxyl group is preferably in the 2-, 3- or 4-position, particularly preferably in the 2-position, of the heterocyclic substituent. This heterocyclic substituent is a pyrrolidine radical for n=0 and a piperidine radical for n=1.

In the compounds of the general formula I, the carbon atom carrying the carboxyl group is asymmetric. The compounds according to the invention can therefore be present as a racemate or in the form of their enantiomers.

The present invention relates both to the racemate and also to the (S)- and (R)-enantiomer.

Preferred compounds of the general formula I are 3-(2-carboxypiperidino)sydnone imine, (S)-3-(2-carboxypyrrolidino) sydnone imine and 3-(4-carboxypiperidino)sydnone imine. The hydrochlorides of the said compounds are particularly preferred.

A compound of the general formula I can be prepared by cyclising a compound of the general formula II

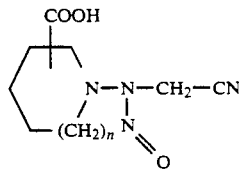

in which n denotes 0 or 1 and optionally converting into a pharmacologically acceptable salt or acid addition salt.

The cyclisation of the compound II to give the compound I is carried out in a suitable organic or inorganic solvent, dispersant or diluent with the addition of a cyclising agent, normally at temperatures from $-10°$ to $40°$ C., in particular $0°$ to $40°$ C., preferably at $0°$ to $20°$ C.

Suitable cyclising agents are those which establish a pH below 3 in aqueous solution, that is to say, for example, mineral acids, such as sulphuric, nitric or phosphoric acid, preferably hydrogen chloride, but also strong organic acids, such as trifluoroacetic acid. The cyclisation is normally carried out with ice-cooling.

0.1 to 10 mol, preferably 1 to 5 mol, of the cyclising agent is used, for example, relative to 1 mol of the compound of the formula II. The cyclising agent is normally employed in excess. The corresponding acid addition salt of the compound I is normally obtained in the cyclisation.

Suitable solvents, dispersants or diluents are, for example: alcohols, for example those having 1 to 8 C atoms, in particular those having 1 to 6 C atoms, preferably those having 1 to 4 C atoms, such as, for example, methanol, ethanol, i- and n-propanol, i-, sec- and tert-butanol, n-, i-, sec- and tert-pentanol, n-hexanol, 2-ethylbutanol, 2-ethylhexanol, iso-octyl alcohol, cyclopentanol, cyclohexanol, methylcyclohexanol (mixture) and benzyl alcohol; ethers, in particular those having 2 to 8 C atoms in the molecule, such as, for example, diethyl ether, methyl ethyl ether, di-n-propyl ether, di-isopropyl ether, methyl n-butyl ether, methyl tert-butyl ether, ethyl propyl ether, di-butyl ether, tetrahydrofuran, 1,4-dioxane, 1,2-dimethoxyethane and bis-β-methoxyethyl ether; oligoethylene glycol dimethyl ethers, such as, for example, tetraglyme or pentaglyme; alkyl carboxylates, in particular those having 2 to 10 C atoms in the molecule, such as, for example, methyl, ethyl, butyl or isobutyl formate, methyl, ethyl, propyl, isopropyl, butyl, iso-butyl or sec-butyl, amyl, isoamyl, hexyl, cyclohexyl or benzyl acetate or methyl, ethyl or butyl propionate; ketones, in particular those having 3 to 10 C atoms in the molecule, such as, for example, acetone, methyl ethyl ketone, methyl n-propyl ketone, diethyl ketone, 2-hexanone, 3-hexanone, di-n-propyl ketone, di-iso-propyl ketone, di-iso-butyl ketone, cyclopentanone, cyclohexanone, methylcyclohexanone, dimethylcyclohexanone, benzophenone and acetophenone; aliphatic hydrocarbons, such as, for example, hexane and heptane, low- and high-boiling petroleum ethers, petroleum spirits and white spirit; cycloaliphatic hydrocarbons, such as, for example, cyclopentane, cyclohexane, methylcyclohexane, tetralin and decalin; aromatic hydrocarbons, such as, for example, benzene, toluene, o-, m- and p-xylene, and ethylbenzene; halogenated aliphatic or aromatic hydrocarbons, such as, for example, methylene chloride, chloroform, carbon tetrachloride, 1,2-dichloroethane, chlorobenzene and dichlorobenzene; hexamethylphosphoramide; sulphoxides, such as, for example, dimethyl sulphoxide; tetramethylene sulphone; and water. Mixtures of different solvents or dispersants may also be used, for example water-methanol or, preferably, ethyl acetate-methanol.

The compounds of the general formula I can form acid addition salts with inorganic or organic acids. For the formation of pharmacologically acceptable acid addition salts, suitable acids are, for example: hydrogen chloride, hydrogen bromide, naphthalenedisulphonic acids, in particular 1,5-naphthalenedisulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. The acid addition salts may be prepared in a customary manner by combining the components, expediently in a suitable solvent or diluent.

In the synthesis of the compound of the formula I, the acid addition salts are normally obtained.

In addition, the compounds of the general formula I can also be present in the form of their internal salts.

The starting compounds of the general formula II may be prepared in a simple manner known per se by the following reaction scheme:

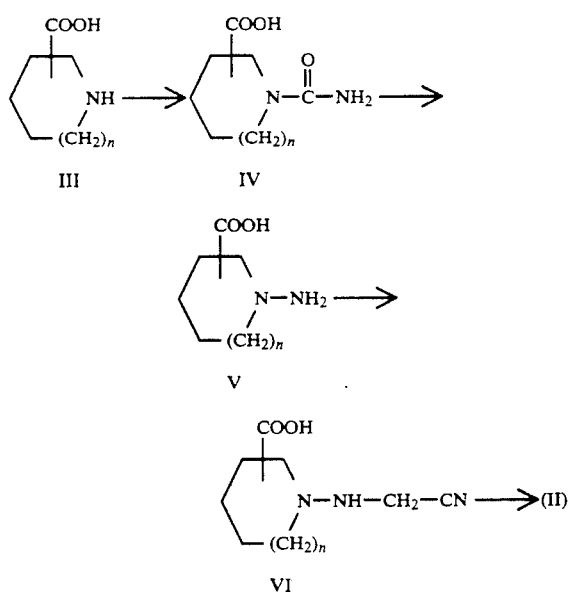

The heterocyclic acid III is accordingly converted into the urea derivative IV, for example with alkali metal cyanate in acidic aqueous solution and this is converted into the hydrazine V by Hofmann degradation. Alternatively, however, the compound of the formula V can also be prepared from the N-nitroso compound of the compound of the formula III by reduction (for 1-aminoproline, for example, Biochemistry 6, 173 (1967)). The compound of the formula V is finally cyanomethylated to give the compound of the formula VI and this is nitrosylated to give the compound of the formula II.

Synthesis of the urea by reaction of an amine with an alkali metal cyanate in acidic aqueous solution is known and described in the literature (see, for example, Houben-Weyl, Methoden der Organischen Chemie (Methods of organic chemistry), 4th edition Vol. E4 page 362). A preferred alkali metal cyanate in this case is potassium cyanate. The Hofmann degradation, i.e. the synthesis of an amine from the corresponding amide by reaction with hypochlorite or hypobromite, is also known from the literature (see, for example, Houben-Weyl, Methoden der Organischen Chemie (Methods of organic chemistry), 4th edition Vol. XI/1 pages 854 et seq.).

Cyanomethylation to give the compound of the formula VI is carried out in a likewise known manner by reaction of the compound of the formula V with formaldehyde and hydrocyanic acid or sodium cyanide in a suitable solvent, for example water. Finally, the nitrosylation is also carried out in a known manner, preferably in water, for example at temperatures from 0° to 10° C. The nitrous acid is in this case normally generated from an alkali metal nitrite, for example sodium nitrite, and hydrochloric acid. It is expedient to adjust the aqueous solution of the precursors to a pH of 1 to 3 with hydrochloric acid and to add the alkali metal nitrite dropwise in the form of an aqueous solution to the stirred and cooled solution of the compound.

The compounds of the general formula III are known and commercially available and/or can be prepared by known methods. The compounds of the general formula III are in particular proline, pyrrolidine-3-carboxylic acid, pipecolinic acid, nipecotic acid and isonipecotic acid.

If the compounds of the general formula III are employed in the form of their, racemates, the compounds of the general formula I according to the invention are also obtained as a racemate. Correspondingly, the synthesis of the (S)- or (R)-forms of the compounds of the general formula I according to the invention is possible by use of the appropriate enantiomerically pure compounds of the general formula III.

The (S)- or (R)-forms of the compounds of the general formula I according to the invention are in addition also accessible from their racemic mixture by the known methods for racemate separation, for example by esterification of the racemate with an optically active alcohol, separation of the resulting diastereomer mixture and basic hydrolysis of the ester.

The compounds of the general formula I and their pharmacologically acceptable salts and acid addition salts have useful pharmacological properties. They are able to release nitric oxide under physiological conditions and thus to increase the antiaggregatory, antiadhesive and muscle-relaxing effect of endothelium-derived relaxing factor (EDRF). They can thus be employed in diseases where the natural endothelial release of NO is not sufficient, such as, for example, angina pectoris and thromboses.

Compared with other sydnone imines, the compounds according to the invention show a slower release of NO, which leads to a uniform and long activity.

The compounds of the formula I and their pharmacologically acceptable acid addition salts can therefore be administered to humans as medicaments by themselves, in mixtures with one another or in the form of pharmaceutical preparations which permit enteral or parenteral use and which contain as the active component an effective dose of at least one compound of the formula I or a salt or an acid addition salt thereof, in addition to customary pharmaceutically innocuous excipients and additives.

The medicaments can be administered orally, for example in the form of pills, tablets, film tablets, coated tablets, hard and soft gelatin capsules, solutions, syrups, emulsions or suspensions, or aerosol mixtures. Administration may, however, also be carried out rectally, for example in the form of suppositories, or parenterally, for example in the form of injection solutions, or percutaneously, for example in the form of ointments or tinctures.

The pharmaceutical preparations can be prepared using pharmaceutically inert inorganic or organic excipients. For the preparation of pills, tablets, coated tablets and hard gelatin capsules, for example lactose, maize starch or derivatives thereof, talc, stearic acid or its salts can be used. Excipients for soft gelatin capsules and suppositories are, for example, fats, waxes, semisolid and liquid polyols, natural or hardened oils etc. Suitable excipients for the preparation of solutions and syrups are, for example, water, sucrose, invert sugar, glucose, polyols, etc. Suitable excipients for the preparation of injection solutions are, for example, water, alcohols, glycerol, polyols or vegetable oils.

The pharmaceutical preparations may contain, in addition to the active compounds and excipients, further additives, such as, for example, fillers, extenders, disintegrants, binders, glidants, wetting agents, stabilisers, emulsifiers, preservatives, sweeteners, colourings, flavourings or aromatisers, buffer substances, and in addition solvents or solubilisers or agents for achieving a depot effect, as well as salts for changing the osmotic pressure, coating agents or antioxidants. They may also contain two or more compounds of the formula I or their pharmacologically acceptable acid addition salts and also other therapeutically active substances.

Examples of other therapeutically active substances of this type are: β-receptor blockers, such as, for example, propranolol, pindolol, metoprolol; vasodilators, such as, for example, carbochromen; tranquilisers, such as, for example, barbituric acid derivatives, 1,4-benzodiazepines and meprobamate; diuretics, such as, for example, chlorothiazide; cardiotonic agents, such as, for example, digitalis preparations; hypotensive agents, such as, for example, hydralazine, dihydralazine, prazosine, clonidine, Rauwolfia alkaloids; agents which lower the fatty acid level in the blood, such as, for example, bezafibrate, fenofibrate; and agents for thrombosis prophylaxis, such as, for example, phenprocoumon.

The compounds of the formula I, their pharmacologically acceptable salts and acid addition salts and pharmaceutical preparations which contain the compounds of the formula I or their pharmacologically acceptable acid addition salts as active compounds can be used in humans for the control or prevention of diseases of the cardiovascular system, for example as anti-hypertensive medicaments in the various forms of high blood pressure, and in the control or prevention of angina pectoris and thromboses. The dosage may vary within wide limits and is to be suited to the individual requirements in each individual case. In general, a daily dose of about 0.5 to 100 mg, preferably 1 to 20 mg, per human individual is suitable for oral administration. For other administration forms, the daily dose, owing to the good absorption of the active compounds, is also in similar amount ranges, i.e. in general also 0.5 to 100 mg/human. The daily dose is normally divided into several, for example 2 to 4, part administrations.

The pharmacological action of the compounds of the formula I was determined by a modified method of Godfraind and Kaba (Arch. Int. Pharmacodyn. Ther. 196, (Suppl) 35 to 49, 1972) and of Schüman et al. (Naunyn-Schmiedeberg's Arch Pharmacol. 289, 409 to 418, 1975). In this connection, spiral strips of the pulmonary artery of the guinea-pig are depolarised with 40 mmol/l of potassium after equilibration in calcium-free Tyrode solution. An addition of 0.5 mmol/l of $CaCl_2$ then induces a contraction.

The relaxing action of the test substance is determined by cumulative addition in ½ log 10 stepped concentrations. From the concentration-effect curve (abscissa: -log mol/l of test substance, ordinate: % inhibition of the maximum contraction, average value of 4 to 6 vessel strips), the concentration of the test substance is determined which inhibits the contraction by 50% (= $IC_{50}$, mol/l). The duration of action of the test substance is given by the time which is needed after the addition of the test substance until the starting value is obtained again. The values thus obtained are indicated in the following table.

| Compound from | $IC_{50}$ | Duration of action in minutes |
|---|---|---|
| Example 1 | $6 \times 10^{-6}$ | >300 |
| Example 2 | $2.4 \times 10^{-5}$ | >300 |
| Example 3 | $2 \times 10^{-5}$ | >300 |
| Comparison substances | | |
| SIN-1 | $1 \times 10^{-6}$ | 90 |
| Molsidomine | $3 \times 10^{-4}$ | 120 |

SIN-1 = N-ethoxycarbonyl-3-morpholinosydnone imine
Molsidomine = 3-morpholinosydnone imine hydrochloride

EXAMPLES 1. 3-(2-Carboxypiperidino)sydnone imine hydrochloride

A mixture of 129 g of (D,L)-pipecolic acid, 500 ml of water and 122 g of potassium cyanate is briefly heated to the boiling point and cooled in an ice bath after 5 min. and rendered acidic with 200 ml of 50% strength sulphuric acid. The resulting urea (1-aminocarbonyl piperidine-2-carboxylic acid) is filtered off with suction and dried.

Yield: 149 g

M.p. 148° C. (dec.) 12.9 g of this compound and 12.6 g of KOH are dissolved in 40 ml of water, cooled to 5° C. and treated with 32.6 g of a 30% strength potassium hypochlorite solution and the mixture is stirred at increasing temperature for 15 hours. The excess hypochlorite is destroyed by addition of 3 g of sodium sulphite. The mixture is filtered, cooled and rendered acidic with 22.5 ml of a 10 M hydrochloric acid. After adding 6.5 g of potassium cyanide, the mixture is adjusted to pH=7.6 with hydrochloric acid and 5.9 g of a 38% strength formalin solution are added. The pH of the mixture is adjusted to 7-7.5 with sodium carbonate solution and the mixture is stirred at room temperature for 15 hours. The mixture is cooled in an ice bath, rendered acidic with 10 M hydrochloric acid (pH=1), treated with 6.9 g of sodium nitrite and stirred at increasing temperature for 5 hours. 100 ml of ethyl acetate are then added and the aqueous phase is adjusted to pH=1. The ethyl acetate phase is separated off, dried over sodium sulphate under nitrogen and mixed with 25 ml of a 30% strength isopropanolic hydrochloric acid. After allowing to stand overnight at room temperature, the solid which has deposited is removed by filtration and the filtrate is concentrated. The oily residue is dissolved in 50 ml of methanol and the solution is heated with active carbon, filtered and diluted with 800 ml of ethyl acetate. A solid crystallises out of this solution after some time, and is filtered off with suction and dried.

Yield: 7.4 g

M.p. 122° C. (dec.)

2. 3-(4-Carboxypiperidino)sydnone imine hydrochloride was obtained in an analogous manner from isonipecotic acid and melts at 172° C. with decomposition.

3. (S)-3-(2-Carboxypyrrolidino)sydnone imine hydrochloride was obtained in an analogous manner from L-proline.

M.p. 142°-144° C. (dec.)

Rotation: $a_D{}^{20} = -100°$ (water; c=1.0)

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Substituted 3-aminosydnone imines of the formula

I

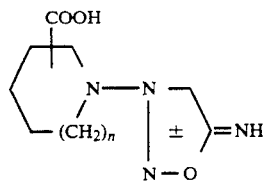

in which n denotes 0 or 1, or their pharmacologically acceptable salts or acid addition salts.

2. Substituted 3-aminosydnone imines according to claim 1, characterised in that the carboxyl group is in the 2-position of the heterocyclic substituent.

3. 3-(2-Carboxypiperidino)sydnone imine hydrochloride.

4. (S)-3-(2-Carboxypyrrolidino)sydnone imine hydrochloride.

5. 3-(4-Carboxypiperidino)sydnone imine hydrochloride.

6. 3-(2-Carboxypiperidino)sydnone imine.

7. (S)-3-(2-Carboxypyrrolidino)sydnone imine.

8. 3-(4-Carboxypiperidino)sydnone imine.

* * * * *